United States Patent [19]

Fleenor

[11] Patent Number: 5,041,110
[45] Date of Patent: Aug. 20, 1991

[54] CART FOR MOBILIZING AND INTERFACING USE OF AN ELECTROSURGICAL GENERATOR AND INERT GAS SUPPLY

[75] Inventor: Richard P. Fleenor, Denver, Colo.

[73] Assignee: Beacon Laboratories, Inc., Denver, Colo.

[21] Appl. No.: 377,528

[22] Filed: Jul. 10, 1989

[51] Int. Cl.$^5$ .............................................. A61B 17/36
[52] U.S. Cl. ........................................ 606/34; 606/40; 606/37; 606/39
[58] Field of Search .................................. 606/10–13, 606/17–20, 23, 27, 28, 32–40

[56] References Cited

U.S. PATENT DOCUMENTS

| | | | |
|---|---|---|---|
| 2,510,205 | 6/1950 | Baird | 219/8 |
| 2,618,267 | 11/1952 | Hanriot | 128/303.14 |
| 2,708,933 | 5/1955 | August | 128/303.14 |
| 2,828,747 | 4/1958 | August | 128/303.14 |
| 3,578,939 | 5/1971 | Green | 219/74 |
| 3,834,392 | 9/1974 | Lampman et al. | 128/303.14 |
| 4,040,426 | 8/1977 | Morrison, Jr. | 128/303.17 |
| 4,060,088 | 11/1977 | Morrison, Jr. et al. | 128/303.17 |
| 4,072,152 | 2/1978 | Linehan | 606/23 |
| 4,100,390 | 7/1978 | Jackson | 219/74 |
| 4,196,734 | 4/1980 | Harris | 606/38 X |
| 4,209,018 | 6/1980 | Meinke et al. | 606/38 X |
| 4,562,838 | 1/1986 | Walker | 128/303.14 |
| 4,573,466 | 3/1986 | Simada et al. | 606/11 |
| 4,640,279 | 2/1987 | Beard | 128/303.14 |
| 4,781,175 | 11/1988 | McGreevy et al. | 606/40 |
| 4,901,720 | 2/1990 | Bertrand | 606/40 |

OTHER PUBLICATIONS

"The Argon Beam Coagulator. A User Experience Profile", Bard Electro Medical Systems, Inc.

Primary Examiner—Robert A. Hafer
Assistant Examiner—Kerry Owens
Attorney, Agent, or Firm—Sheridan, Ross & McIntosh

[57] ABSTRACT

A cart (10) is provided for conveniently carrying an electrosurgical generator (14) and for providing electricity from the generator (14) and inert gas from gas tanks (66–68) to an electrosurgical pencil (40). The cart (10) comprises a platform (12) constructed and arranged to receive any electrosurgical generator (14). A wheeled support structure (16) allows storage and transport of the necessary components for operating the generator (14) and the pencil (40). The cart (10) contains space for receiving gas tanks (66–68) and the connections for transferring the gas from the tanks (66–68) to the pencil (40) at a desired flow rate. The cart (10) also provides the electrical connections to provide electricity to the generator (14) and to the pencil (40) simultaneously with the inert gas.

19 Claims, 4 Drawing Sheets

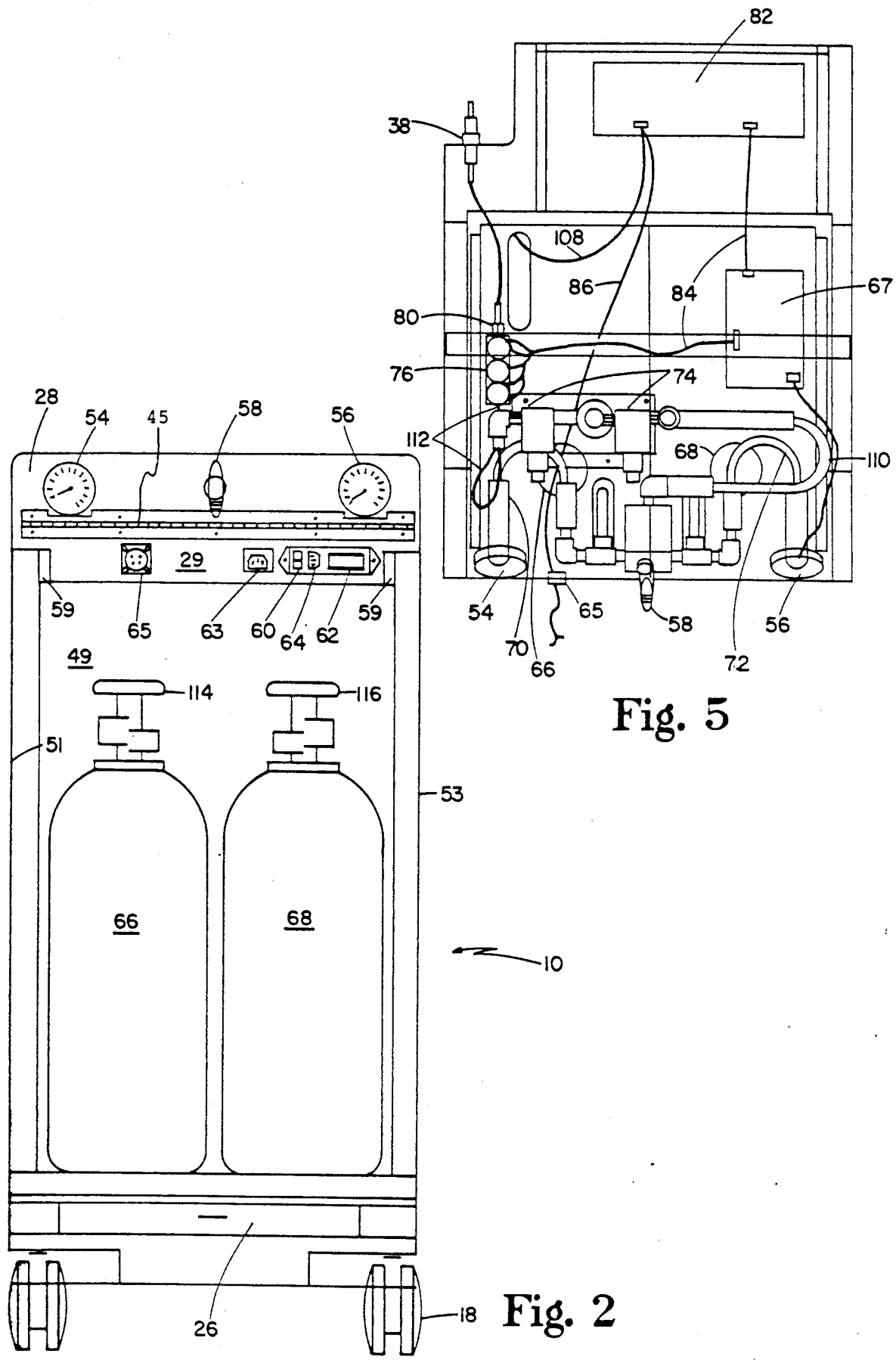

CART FOR MOBILIZING AND INTERFACING USE OF AN ELECTROSURGICAL GENERATOR AND INERT GAS SUPPLY

TECHNICAL FIELD OF THE INVENTION

This invention relates in general to electrosurgical devices, and in particular to an apparatus for mobilizing an electrosurgical generator and for conveniently allowing the use of an inert gas with the generator.

BACKGROUND OF THE INVENTION

Electrosurgical generators have long been used for the control of bleeding and for making incisions in major surgery. Currently, there are approximately 22 million surgeries conducted every year in the United States, and of those 22 million roughly 18 million are conducted using electrosurgical techniques. The use of electrosurgical generators requires that an electrosurgical pencil be interconnected to the generator. An electrosurgical pencil comprises an insulated handle with an electrode therein for passing an electric charge to a patient. The generator provides a source of electric current to the electrode of the pencil which is then used, for example, to cut tissue or coagulate blood.

Unfortunately, the use of electricity in a surgical environment has occasionally caused serious injury to the patient and the surgical personnel. When anesthetics commonly used were of a flammable or explosive nature, the uncontrolled emission of electric current often ignited the anesthetic. Since anesthetics are generally no longer flammable, the risk of their ignition has been greatly reduced.

It has been found that the use of an inert gas (such as Argon) tends to actually enhance (rather than insulate) the flow of electricity in electrosurgery through ionization of the inert gas atoms. Inert gas enhanced electrosurgery allows coagulation without excessively drying tissue, and thus is a valuable surgical tool. Unfortunately, gas enhancement is a substantially untapped surgical resource due to the lack of a device that combines the inert gas with the electric charge.

The current state of the art reflects the use of electrosurgery generally without the use of an enhancing inert gas. There are different electrosurgical generators and electrosurgical pencils currently manufactured that do not incorporate inert gas. These generators are typically separate units that are placed on tables or stands in the operating room. There has been no device that allows the adaptation of the existing generators for use with inert gas for enhanced electrosurgery. One device (System 6000 by Bartcher Electro-Medical Systems, Inc.) does combine an inert gas supply and generator for electrosurgery but does not generally meet the needs of the industry. Thus, there is a need for a method and apparatus to mobilize an electrosurgical generator and allow inert gas enhanced electrosurgery using an existing generator.

SUMMARY OF THE INVENTION

The present invention disclosed herein comprises a method and apparatus for mobilizing an electrosurgical generator and combining therewith the benefits of inert gas enhancement. The present invention allows the convenient consolidation of a multiplicity of parts needed to conduct electrosurgery with an inert gas.

In accordance with one aspect of the invention, a cart for mobilizing an electrosurgical generator comprises a platform for receiving the electrosurgical generator. The platform is fixed to a wheeled support structure for ease of transport. Outlets are provided on the cart for interconnecting an electrosurgical pencil to an inert gas supply also containable within the support structure. Built within the support structure are facilities for receiving and storing inert gas tanks for use with the electrosurgical pencil. A power supply is attached within the platform to supply voltage to a logic board and to a flow control valve. Integral to the cart is a control logic panel for operatively interconnecting the pencil, the gas supply, the power supply and the generator.

In use, the cart is connected to an external source of power such as a wall electrical outlet. A foot activated control is connected to the generator through the control logic panel and an outlet on the cart. By pressing the foot control a surgeon is able to activate the simultaneous flow of gas and electricity to the electrosurgical pencil. Thus enhancement of electrosurgery by inert gas is provided by the apparatus of the present invention. The platform of the present invention is capable of accepting any of the electrosurgical generators currently in use without any other special or expensive additions.

BRIEF DESCRIPTION OF THE DRAWINGS

For a more complete understanding of the present invention and for further advantages thereof, reference is now made to the following Detailed Description taken in conjunction with the accompanying Drawings in which:

FIG. 2 is a rear elevation of the cart of FIGURE 1;

FIG. 5 is a top plan view of the platform of the present invention with the top surface removed.

DETAILED DESCRIPTION OF THE INVENTION

Figure 1:
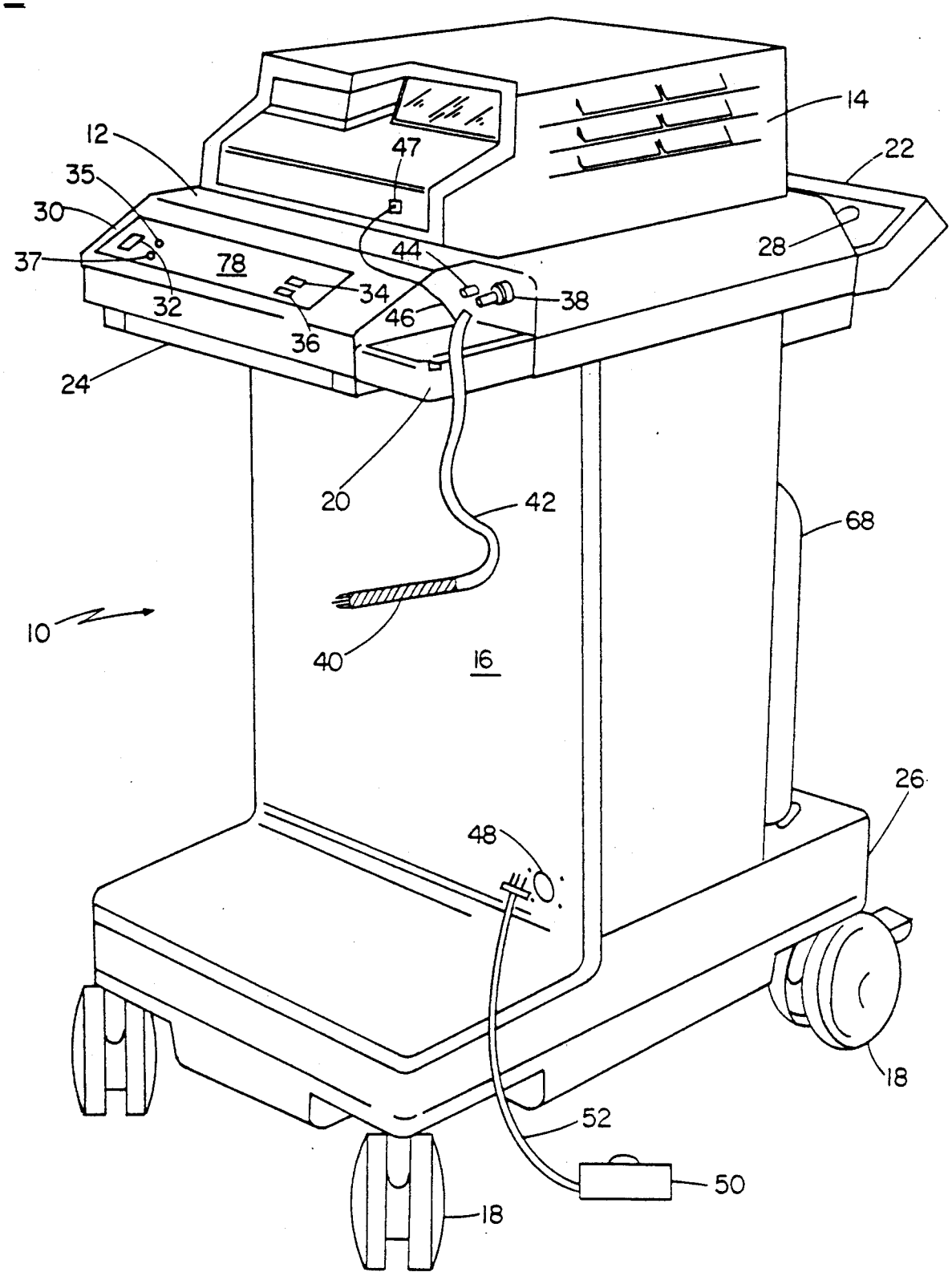
FIG. 1 is an isometric view of a cart constructed in accordance with the preferred embodiment of the present invention.

Referring to FIG. 1, an electrosurgical cart constructed in accordance with the preferred embodiment of the present invention is generally identified by the reference numeral 10. The cart 10 comprises a platform 12 constructed and arranged to receive an electrosurgical generator 14. The generator 14 may comprise any electrosurgical generator currently manufactured, which may, due to the benefits of the cart 10, be used thereon in conjunction with an inert gas.

Fixed to the platform 12 is a support structure 16 which is provided with wheels 18 to facilitate mobility thereof. The cart 10 is also provided with a front handle 20 and a rear handle 22 which allows an operator to easily push and/or pull the cart 10. In the preferred embodiment, the rear handle 22 may be angled upwardly with reference to horizontal to provide a convenient location for wrapping an external source power cord while not in use.

A top drawer 24 may be provided for the storage of instruction manuals etc., and a lower drawer 26 may be provided for the storage of associated cables and controls. Conveniently located on a first end wall 28 of the platform 12 are controls and gauges for operation of the cart 10 and the generator 14, as will be subsequently described in greater detail. Similarly, located on a second end wall 30 of the platform 12 is a control panel 78 containing visual indications of, for example, a selected flow rate by an LED display 32, a low gas indicator light 34, an out of gas indicator light 36, an increase flow rate control button 35 and a decrease flow rate control button 37. Fixed to the panel 78 inside the platform 12 is a control logic panel 82, as will be subsequently described in greater detail. The lights 34 and 36 may also be combined with audible signals to assist an operator in rapid perception of the low or out of gas status.

Conveniently located on the platform 12 is a gas coupling 38 (which may be, for example, a panel mount gas quick coupling such as is available from Colder Products Co., St. Paul, Minn., under their part number LCD 160-04) for installing an electrosurgical pencil 40 by a gas tube 42. Positioned proximate the coupling 38 is an optional coupling 44 which may be used with an electrosurgical pencil having a finger activated control thereon (not shown).

An electrical connection wire 46 exits the gas tube 42 proximate the coupling 38 for connection to the electrosurgical generator 14 at an outlet 47 thereon. Although not shown, it is to be understood that a return pad must be used in conjunction with the generator 14 and the pencil 40 to complete a circuit formed between the generator 14, the pencil 40 and a patient.

Also conveniently located on the support structure 16 is a four-pronged outlet 48 for interconnection of a foot activated control 50. The foot control 50 may comprise, for example, a single pedal foot switch such as is available from Linemaster Switch Corp. of Woodstock, Conn., under their number 591-EX. The foot activated control 50 is removably attached to the outlet 48 by a power cable 52. The foot activated control 50 allows an operator, such as a surgeon, to simultaneously provide current and inert gas to the pencil 40 without manipulating a multiplicity of separate control devices. Although not shown, it is to be understood that the foot control 50 may be an infrared transmitter coupled to the structure 16 by an infrared receiver therein without the need of a power cable 52 which may provide greater operating room freedom.

The platform 12 may be opened about a hinge 45 (FIG. 2) along the first end wall 28. The platform 12 must be secured from accidental opening thereof about the hinge by an appropriate latch device (not shown) which may be located proximate the second end wall 30. Also, slides 59 (FIG. 4) may be provided to allow the platform 12 to slide horizontally forward by pulling on the handle 20 or by pushing on the handle 22. By sliding the platform 12 forward, inert gas tanks 66-68 (FIGS. 2 and 4) may be changed with greater ease than if the platform 12 did not slide. Appropriate slide locks (not shown) will be provided to prevent accidental sliding of the platform 12.

Referring to FIG. 2, a rear elevation of the cart 10 is shown revealing that the structure 15 comprises a three sided container with a front wall 49, first and second side walls 51 and 53 and an open back. Located within the first end wall 28 of the platform 12 is a first pressure gauge 54 and a second pressure gauge 56. The gauges 54-56 may comprise, for example, two inch gauges registering 0-3000 psi such as are available from McDaniel Controls, Inc. of Luling, La., under their part number TNU, are provided to allow an operator or an assistant to the operator (such as a nurse) to monitor the pressure within the inert gas tanks 66-68 in order to choose the appropriate tank for surgical use. A three-way valve 58 is also conveniently located on the wall 28 to allow selection of the inert gas tank 66 or 68. Depending from the gauges 54-56 and the valve 50 are appropriate hoses and connectors (FIG. 5) for attachment to the tanks 66-68, as will be subsequently described in greater detail.

Also located on a panel 29 below the first end wall 28 is a power switch 60 and a power selector 62. An external power source (not shown) may be plugged into the power selector 62 via an electrical inlet 64 which may comprise an improved three prong International Electric Code (IEC) socket. The power selector 62 may comprise, for example, a power entry module capable of selectively receiving 100, 120, 220 or 240 volts of alternating current (VAC), such as is available from Corcom, Inc. of Libertyville, Ill. under their part number 6 Vm4S. A power supply 67 is provided to convert any of the incoming VAC's from the power selector 62 to twelve volts of direct current (VDC). The power supply 67 may be, for example, a power supply such as is available from Condor, Inc. of Oxnard, Calif. under their model number HC12-3.4-A. The twelve VDC is required by the control logic panel 82 and a flow control valve assembly 76 (FIG. 5). The power switch 60 provides the capability through, for example, a toggle switch, to turn the power to the entire cart 10 on or off.

Adjacent the power switch 60 is a power outlet 63, which may comprise a standard three prong IEC socket, for providing the electrical power to the generator 14. Also on the panel 29 is a four prong outlet 65 which is used in conjunction with a power cable and an inlet (neither shown) on the generator 14. The outlet 65 allows a convenient and orderly interconnection between the foot activated control 50 and the generator 14. By interconnecting the generator 14 and the control 50 through the outlet 65, an operator is afforded the benefits of the simultaneous control of electricity and inert gas.

Figure 3:
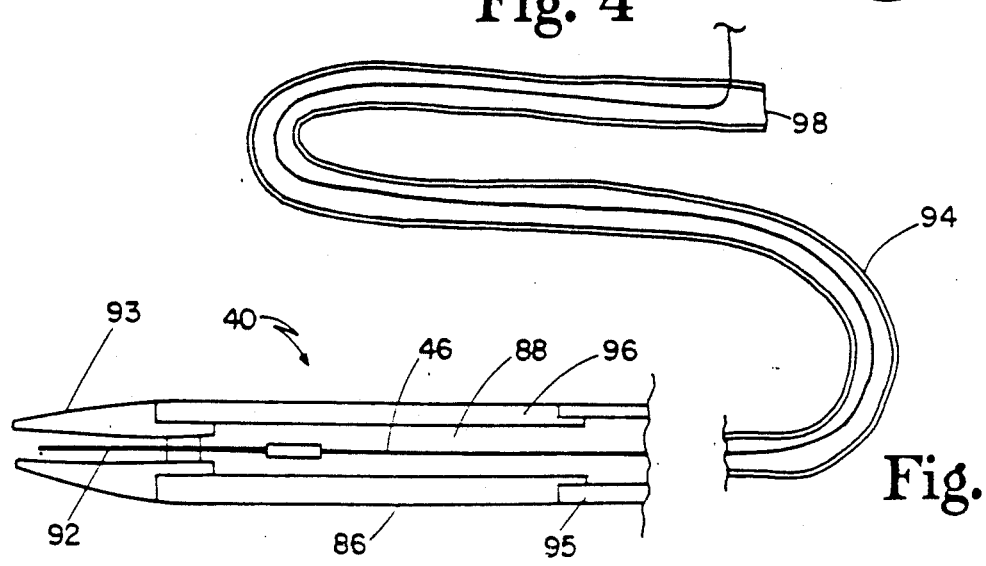
FIG. 3 is a cross-sectional view of an electrosurgical pencil of the present invention.

Referring to FIG. 3, a cross-sectional view of an electrosurgical pencil 40 for use with the Cart 10 is illustrated. The pencil 40 comprises a plastic case 86 of an insulating material which is generally cylindrical in shape. Within the hollow passageway 88 of the case 86 is the electrical wire 46 through which electricity passes to a tungsten electrode 92. A ceramic tip 93 in the general shape of a hollow frustum surrounds the electrode 92 and serves to help direct the inert gas therearound. A flexible gas tube 94 is connected at a first end 95 to an inlet end 96 of the plastic case 86. The tube 94 is then connected at a second end 98 to the coupling 38 on the platform 12. The tube 94 is actually the same size throughout its length and is shown broken and in different sizes for the sake of clarity. The wire 46 exits the gas tube 94 prior to the second end 98 allowing interconnection to the electrosurgical generator 14 through the outlet 47 thereon. Thus, electricity is allowed to flow from the generator 14 through the wire 46 to the electrode 92. Simultaneously, gas flows through the gas tube 94 to surround the wire 46 and the electrode 92. The electrode 92 ionizes the inert gas which enhances the function of the pencil 40 to coagulate the blood of a patient. The enhancement of electrosurgery with an inert gas has been shown to lower the amount of tissue desiccation over non-gas electrosurgery. Thus inert gas enhanced electrosurgery provides a technique allowing surgeons to obtain more blood coagulation with less tissue desiccation and less blood loss.

Figure 4:
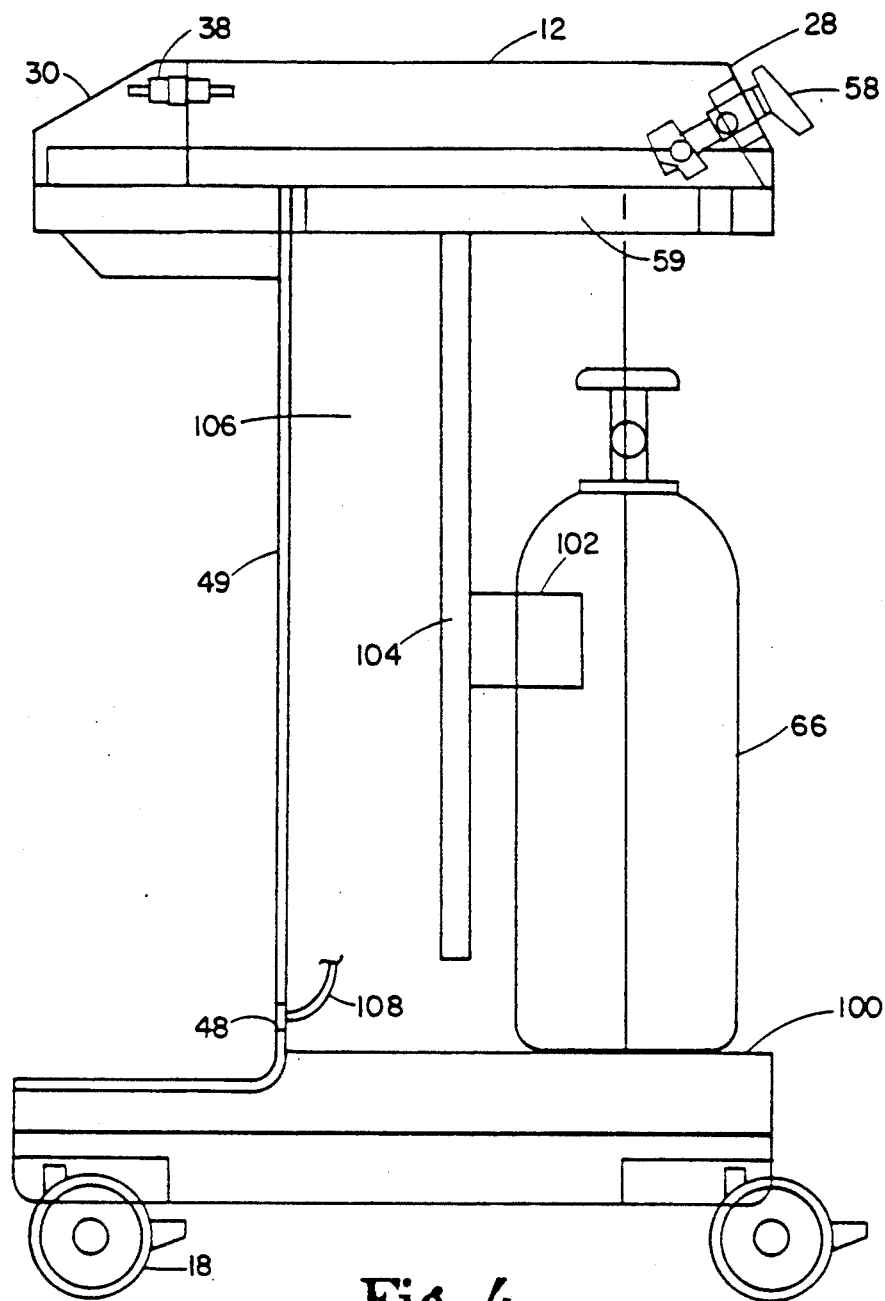
FIG. 4 is a cross-sectional view of the cart of the present invention.

Referring to FIG. 4, a side view of the cart 10 is shown with the first side wall 51 removed for clarity. In the preferred embodiment, located within the cart 10 and fixed to the platform 12 are the various controls and interconnections (FIG. 5) required to operate the electrosurgical generator 14 and the pencil 40. Conveniently located toward the rear of the cart 10 are the first and second gas tanks 66 and 68 which may contain an inert gas, preferably argon.

The tanks 66-68 sit within depressions formed in a base plate 100 of the cart 10. The tanks 66-68 are held in place by support brackets 102 which are fixed to a middle wall 104. The wall 104 is connected on each end thereof to the first and second side walls 51-53 to provide lateral support to the cart 10. Between the front wall 49 and the middle wall 104 is a cavity 106 within which runs a power interconnect cable 108. The cable 108 connects the outlet 48 for the foot control 50 through the control logic panel 82 (FIG. 5) to the four prong outlet 65 (FIG. 2).

Referring to FIG. 5, a detailed top plan view of the platform 12 is shown with a top surface thereof removed for the sake of clarity. The pressure gauges 54-56 are connected to the gas tanks 66-68 by gas hoses 70 and 72, respectively. The hoses 70-72 also connect the tanks 66-68 to the three-way valve 58. A hose 110 connects the three-way valve 58 into a two stage regulator 74 which may comprise, for example, a brass regulator such as is available from Victor Equipment Company of Denton, Tex. under their part number TBD. The regulator 74 provides a pressure drop in a first stage thereof from the tanks 66-68 (which are approximately 2400 PSI) to 100 PSI. A second stage of the regulator 74 further drops the pressure from 100 PSI to 30 PSI which is appropriate for use with the generator 14 and the pencil 40. Although not shown, sensors may be positioned around the regulator 74 to signal the low gas indicator 34 and the out of gas indicator 36 on the control panel 78.

Interconnected to the regulator 74 through a hose 112 is a flow control valve assembly 76. The flow control valve assembly 76 may comprise, for example, three solenoid valves such as are available from Automated Systems Product of Simi Valley, Calif. under their part number 63-211-N103-20, which allow a gas flow rate of 4, 6, 8, 10 or 12 liters per minute. The flow rate is selectable from the buttons 35 and 37 located on the control panel 78.

An outlet 80 on the valve assembly 76 directs the selected flow rate of gas to the coupling 38 and thence to the pencil 40. The flow control valve assembly 76 is interconnected to the control logic panel 82 via electrical wires 84 through the power supply 67. The control logic panel 82 may comprise, for example, an arrangement of printed circuit boards capable of coordinating a release of the flow of gas and electricity by a signal from the foot control 50. The electrosurgical generator 14 is interconnected to the control logic panel 82 and thus the foot control 50 by a wire 86 and to the four prong outlet 65, as previously described.

In operation, the platform 12 would be slid forward along its provided slides 59 to allow insertion of the gas bottles 66 and 68. The gas lines 70 and 72 would be connected to the tanks 66-68 and the gas would be allowed to flow therethrough by the opening of valves 114 and 116 (FIG. 2) which are integral with the tanks 66-68. Gas would thus flow to the pressure gauges 54-56 and would further be allowed to flow, based upon the positioning of the three-way valve 58, to the regulator 74 for the appropriate pressure drops.

From the regulator 74, gas would enter the flow control valve 76 which would allow flow to the coupling 38 based upon the selected flow rate upon receipt of a signal from the foot control 50. Electrical power would be provided to the cart 10 through the electrical inlet 64. The power switch 60 allows electricity to be available upon need. Upon activation of the foot control 50 by a surgeon, electricity and gas would flow to the electrosurgical pencil 40 for use in surgery to coagulate blood.

Figure 6:
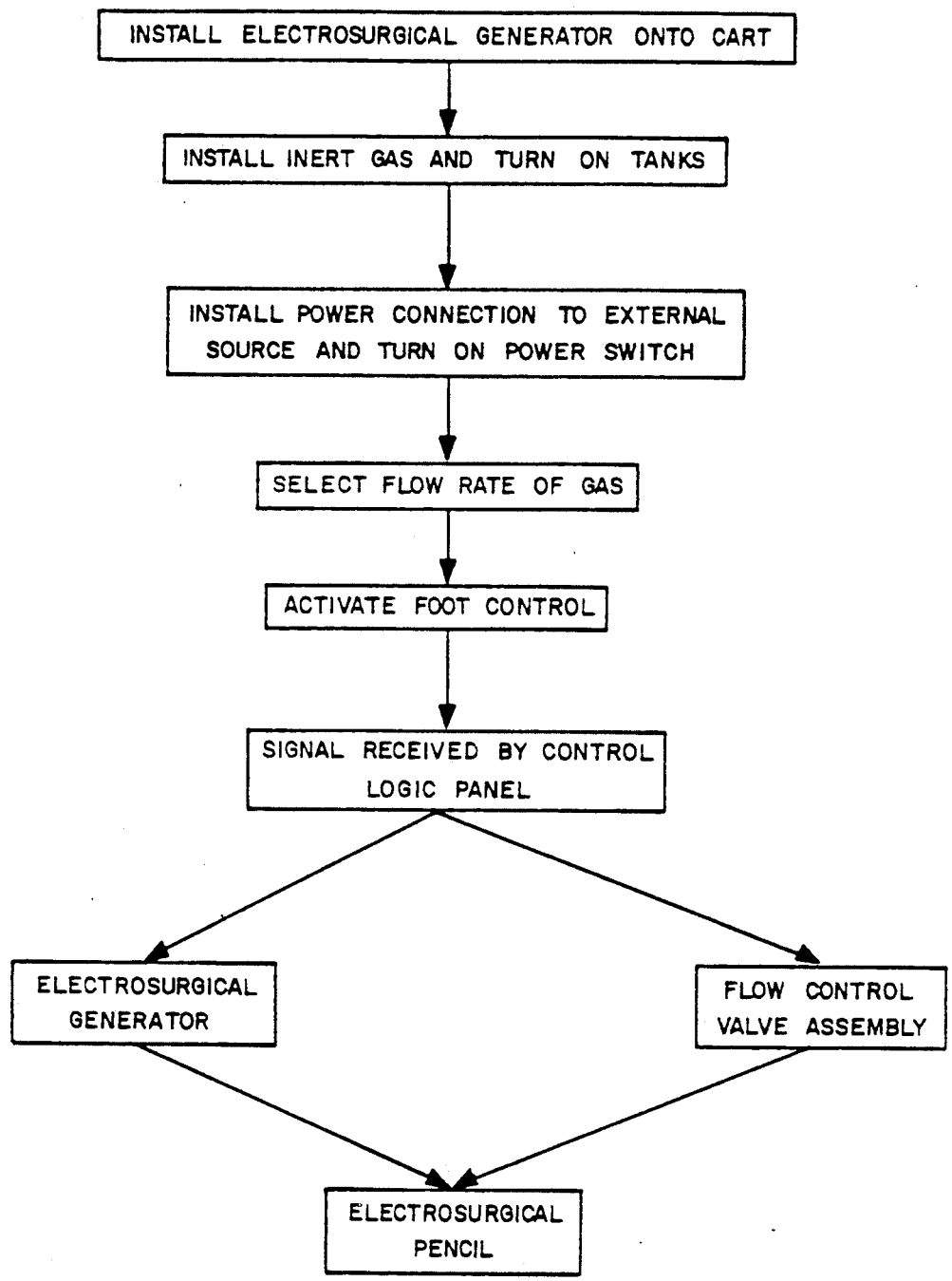
FIG. 6 is a flow chart of the operation of the cart of the present invention.

Referring to FIG. 6, a flow chart schematically showing the operation of the cart 10 is illustrated. The first step in the operation of the cart 10 is, of course, to install any electrosurgical generator onto the platform 12 of the cart 10. The inert gas tanks 66-68 are installed into the cart 10 and the integral valves 114 and 116 thereon opened to activate flow of the gas. A power cord is plugged into the electrical inlet 64 and an external power source, followed by turning on the power switch 60. An operator then selects the desired gas flow rate by depressing the control buttons 35 and/or 37 on the control panel 78. The operator activates the foot control 50 which sends a signal to the control logic panel 82 which simultaneously signals the electrosurgical generator 14 (to start the flow of electricity) and the flow control valve assembly 76 (to start the flow of inert gas). The operator may then perform the desired surgical procedure on a patient. By monitoring the control panel 78 and the pressure gauges 66-68, the cart 10 may be operated efficiently for inert gas enhanced electrosurgery.

Although the present invention has been described with respect to a specific preferred embodiment thereof, various changes and modifications may be suggested to one skilled in the art, and it is intended that the present invention encompass such changes and modifications as fall within the scope of the appended claims.

What is claimed is:

1. A cart for mobilizing and operatively interfacing a standard electrosurgical generator, an electrosurgical pencil and at least one inert gas receptacle to permit an operator to conduct gas enhanced electrosurgery, comprising:

a wheeled support structure;

means, mounted on said wheeled support structure adapted for receiving said at least one inert gas receptacle;

means, mounted on said wheeled support structure, adapted for receiving said standard electrosurgical generator and comprising an exposed upper platform for supporting the standard electrosurgical generator;

means, mounted on said wheeled support structure, adapted for receiving said electrosurgical pencil and interconnected to said means for receiving said at least one inert gas receptacle; and control interface means, mounted on said wheeled support structure, interconnected to said means for receiving said at least one gas receptacle and connectable to operator control means, wherein an operator may control the provision of inert gas from the at least one gas receptacle to said electrosurgical pencil and the provision of an electrical output from said standard electrosurgical generator to the electrosurgical pencil to conduct gas enhanced electrosurgery.

2. The cart of claim 1, wherein said means for receiving said at least one gas receptacle comprises:
   a regulator to control pressure of the inert gas provided to said electrosurgical pencil;
   a valve for controlling the flow rate of the inert gas to said electrosurgical pencil; and
   means to connect said at least one gas receptacle to said regulator, said regulator to said valve and said valve to said means for receiving said electrosurgical pencil.

3. The cart of claim 1, wherein said operator control means comprises a foot activated switch.

4. The cart of claim 1, wherein said means for receiving the pencil comprises a coupling fixed to the cart.

5. The cart of claim 1, wherein said control interface means comprises a control logic panel.

6. The cart of claim 1, wherein said platform comprises slide means for horizontally sliding said platform relative to said wheeled support structure, wherein replacement of said at least one inert gas receptacle is accommodated.

7. The cart of claim 1, wherein said platform comprises a hinge for opening said platform, wherein access to at least a portion of said means for receiving said at least one inert gas supply is accommodated.

8. The cart of claim 1, further comprising inert gas amount indicator means interconnected to said means for receiving said at least one inert gas receptacle, wherein an indication is provided to an operator when the amount of inert gas in said at least one inert gas receptacle drops below a predetermined value.

9. The cart of claim 1, further comprising outlet means connected to said control interface means and connectable to said standard electrosurgical generator for transmission of an interface signal to coordinate said provision of inert gas and electrical output to said electrosurgical pencil to conduct gas enhanced electrosurgery.

10. The cart of claim 1, further comprising first outlet means connectable to an external power source.

11. The cart of claim 1, further comprising pressure indicating means interconnected to said means for receiving said at least one inert gas receptacle, wherein the internal pressure of said at least one inert gas receptacle is indicated to an operator.

12. The cart of claim 1, further comprising means interconnected to said means for receiving said at least one inert gas receptacle for controlling selective interconnection of a single inert gas receptacle to said means for receiving said electrosurgical pencil.

13. The cart of claim 2, further comprising flow rate control means interconnected to said valve, wherein an operator may selectively control the flow rate of the inert gas provided to said electrosurgical pencil.

14. The cart of claim 3, wherein said foot activated switch is operatively interconnected to the cart by cable means.

15. The cart of claim 3, wherein said foot activated switch operatively interconnected to the cart by infrared means.

16. The cart of claim 13, further comprising flow rate indicator means interconnected to said means for receiving said at least one inert gas receptacle, wherein the flow rate of the inert gas provided to said electrosurgical pencil is indicated to an operator.

17. The cart of claim 10, wherein said first outlet means is interconnected to said control interface means to provide power thereto.

18. The cart of claim 17, further comprising means interconnected between said first outlet means and said control interface means for converting an alternating current received from said external power source to a direct current.

19. The cart of claim 10, further comprising second outlet means interconnected to said first outlet means and connectable to said standard electrosurgical generator for providing power thereto.

* * * * *